United States Patent [19]

Finsterwalder et al.

[11] 4,160,382
[45] Jul. 10, 1979

[54] SAMPLE TAKING DEVICE FOR TOXIC AND/OR RADIOACTIVE SUBSTANCES

[75] Inventors: Lorenz Finsterwalder; Horst Zeh, both of Karlsruhe; Ulrich Schaarschmidt, Stutensee, all of Fed. Rep. of Germany

[73] Assignee: Gesellschaft zur Wiederaufarbeitung von Kernbrennstoffen mbH, Eggenstein-Leopoldshafen, Fed. Rep. of Germany

[21] Appl. No.: 834,253

[22] Filed: Sep. 16, 1977

[51] Int. Cl.² .............................................. G01N 1/10
[52] U.S. Cl. ................................... 73/422 R; 141/329
[58] Field of Search ............. 73/421 R, 421 A, 422 R; 141/329, 130

[56] References Cited

U.S. PATENT DOCUMENTS

| 2,693,705 | 3/1954 | Casler et al. | 73/421 B |
| 2,968,183 | 1/1961 | Hannaford et al. | 73/421 R |
| 3,383,923 | 5/1968 | Conche et al. | 73/421 B |

Primary Examiner—S. Clement Swisher

Attorney, Agent, or Firm—Spencer & Kaye

[57] ABSTRACT

Apparatus for taking samples of toxic and/or radioactive liquid substances by introducing such substances into sample vessels, the apparatus including a holder for holding such a vessel, at least one needle head filling system composed of upwardly pointing hollow needles for introducing a sample of one such substance into such a vessel at a filling position, and inlet and outlet conduits for pneumatically conveying vessels to or from the holder at a transfer position, with the holder being composed of a turntable having a sleeve for accommodating such vessel and mounted to undergo rotary movement to convey a sample vessel held in the sleeve between the filling and transfer positions, and with the apparatus further including a stand supporting the filling system below the holder, and a lifting device connected for imparting a translational movement to the holder to bring a vessel in the holder to operative association with the filling system, the lifting device being arranged such that the translational movement which it produces is independent of the rotary movement of the turntable.

8 Claims, 4 Drawing Figures

SAMPLE TAKING DEVICE FOR TOXIC AND/OR RADIOACTIVE SUBSTANCES

BACKGROUND OF THE INVENTION

The present invention relates to a sample taking device, for toxic and/or radioactive substances, for guiding a sample vessel in a holder to one of a plurality of needle head filling systems having upwardly oriented hollow needles and to a feeder and discharge line for putting the sample vessel into or taking it out of the holder.

Sample taking devices capable of taking samples from individual processing vessels are required for monitoring and controlling processes, for example during reprocessing of irradiated nuclear fuels. In addition to dissolved toxic and/or radioactive substances, the fluids involved in such processes frequently contain greater or lesser amounts of solid components consisting of undissolved fuel remnants, fission product noble metals or degradation products of the extraction agent. These solid components are deposited at the surfaces of the sample taking systems in contact with the surrounding medium and the radiation emanating from them increases the difficulties attendant to the maintenance and repair of the sample taking devices.

SUMMARY OF THE INVENTION

It is an object of the present invention to provide a sample taking device which is particularly suitable for process monitoring and control in the reprocessing of irradiated nuclear fuels and in which the sensitive parts of the device are kept free of contamination and, during the required decontamination measures, free of cleansing agent.

These and other objects are achieved, according to the present invention, by disposing the needle head filling system or systems on a stand below the holder, forming the holder of a turntable with a sleeve for holding the sample vessel, the turntable being movable over the needle head filling systems and the intake and discharge lines, mounting the turntable and its rotary shaft by means of a lifting device to be movable in a translational manner, and making the rotary and lifting movements independent of one another.

According to one feature of the invention, the needle head filling systems are arranged on the circumference of a stand in such a manner that the sleeve holding the sample vessel can be lowered onto the hollow needles.

According to a further feature of the invention, the turntable is disposed between a cover and disc arrangement having a circular slit and the circular slit can guide the sleeve over the needle head filling systems. In an advantageous manner a detent member is fastened to the cover and disc arrangement so as to be movable via a guide sleeve along the circumference of the shaft parallel to the shaft axis.

According to another advantageous feature of the invention, a circular switching table is provided for setting the turntable, via its shaft, in various positions. In this case the detent member is moved by means of pneumatically actuatable pins.

According to another feature of the invention, the circular switching table and the pressure cylinders for the pins are disposed above a cover plate which delimits the sample taking chamber. In order to provide contamination-free separation, the pins and the shaft are sealed, by means of seals, from the chamber in which the samples are being taken.

With use of a conical needle head with venturi nozzle and upwardly oriented hollow needles, as disclosed in copending, commonly assigned U.S. application Ser. No. 785,182, filed by Horst Zeh, on Apr. 6, 1977, the danger of clogging is almost eliminated and dripping after removal of a sample vessel is prevented. The vertical arrangement also reduces the proportion of undesirable solid components in the sample. Furthermore, the rotary movement and the lifting movement are not coupled together.

According to the present invention, the rotary movement is effected from the top by a pneumatic circular switching table having, for example, eight rotary positions, including a magazine position, six sample taking positions with associated corresponding needle head filling systems and a pneumatic conveyor tube position, which are established by the engagement of a ratchet in the circular switching table. The pneumatic operating cylinder thus always operates against a fixed abutment so that complicated adjustment of terminal switches for the control of the end position is eliminated.

The lifting movement is advantageously also effected from the top via pneumatic cylinders acting on a follower plate, e.g. cover and disc arrangement, with which the holder for the sample vessel and the sample vessel are impaled on the needle head filling systems. Here again the pneumatic cylinders operate against fixed abutments.

During use of the sample taking devices, for example in a reprocessing plant, the sample taking device is installed in a glove box. The cover of this box may then serve, according to a particularly advantageous embodiment of the present invention, as the abutment for the circular switching table and for the lifting cylinders.

By decoupling the lifting movement from the rotary movement it becomes possible to establish mechanical passages in a contamination-tight manner, for example employing 0-ring seals for the rotary movement, and lip seals for the pneumatic cylinders. The passages in the cover of the box are under much less stress than the corresponding passages in the bottom of the box. Since the discharge of the pneumatic conveying tube is also in an upward direction and the rotary and lifting movements are guided through a guide tube flanged into the cover of the box, the entire lower portion of the sample taking devices can be flooded for decontamination purposes without thereby inundating bearings or mechanical passages.

The robust pneumatic drives are furthermore arranged, according to the present invention, at the top and outside of the box so as to be easily accessible and are arranged to operate against fixed abutments. The delicate adjusting of sensitive terminal switches in contaminated regions is thus eliminated. The mechanical passages are therefore disposed in a part of the box which is not under much stress and can be designed to perform the rotary or lifting movements, respectively, in a dependable manner.

DESCRIPTION OF THE PREFERRED EMBODIMENTS

Figure 1:
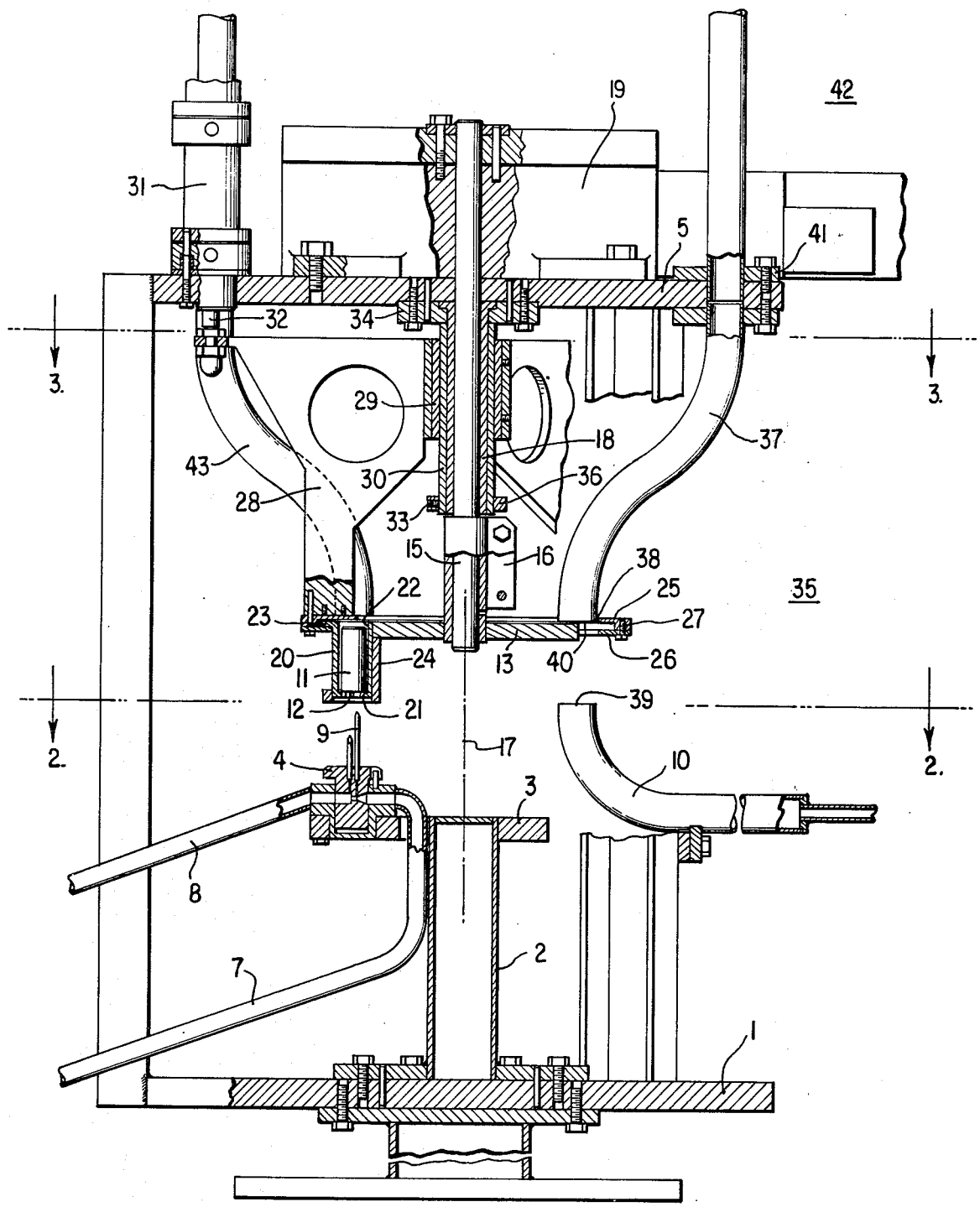
FIG. 1 is a vertical, cross-sectional view of one preferred embodiment of an apparatus according to the invention.

FIG. 1 shows an embodiment of the apparatus according to the invention in a glove box in which a frame 1 carries a stand 2 with a disc-shaped holder 3 for the needle head filling systems 4. The mechanism for performing the lifting and rotary movements of the sample taking device are fastened to a cover plate 5 above the stand 2.

Figure 2:
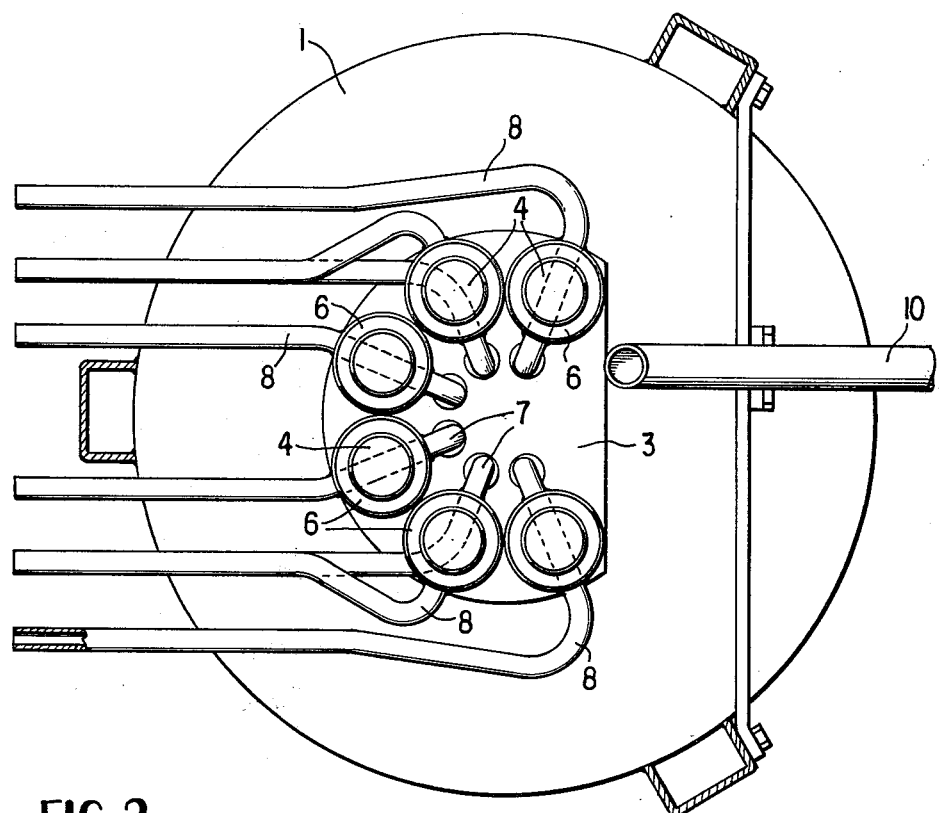
FIG. 2 is a top plan view of the stand equipped with needle head filling systems in the apparatus of FIG. 1, this view being taken along line 2—2 of FIG. 1.

Six different needle head filling systems 4 are on a circumference 6 of disc 3 of stand 2 as can be seen in FIG. 2. Each system 4 is provided with an inlet line 7 and an outlet line 8 for the sample liquid. The needle head filling system 4 shown in FIG. 1 is of the type including a dual hollow needle 9, as disclosed in the above-cited pending application. Referring again to FIG. 2, disc 3 is in the form of a circle having a segment cut off so that space is provided for a compressed air inlet 10. This inlet is part of a pneumatic tube conveying system which will be described in detail with reference to FIG. 1.

A lifting and rotating device must be used to enable the sample vessels 11 to be filled. Each vessel is provided with a bottom seal including a rubber membrane 12 through which the hollow needles 9 can be pushed.

The lifting and rotating device includes a turntable 13 which is fastened at 14 to the lower end of a rotary shaft 15 by means of a mount 16. The axis 17 of shaft 15 is set so that it is coaxial with the center point of the circle defined by disc 3 or its circumference 6. The shaft 15 is supported in a bearing journal 18 which is flanged tightly to the cover plate 5. Shaft 15 protrudes through cover plate 5 and is connected to a circular switching table 19 of known design. This table may be, for example, a Festo Model ST-270 A.

This circular switching table 19 serves to set the sample vessels 11 into the filling, and vessel introduction and removal positions.

Each sample vessel 11 is mounted in a sleeve 20 which carries it to the individual stations. This sleeve 20 has a cylindrical shape and is provided with a opening 21 at its lower end and a fill opening 22 at its upper end. One end of sleeve 20 is further provided with a laterally extending tongue 23 which cooperates with a semicircular sleeve 24 secured to turntable 13 to constitute the holder for sleeve 20. Sleeve 24 is welded to the underside of turntable 13.

Turntable 13 itself together with holder 20 or tongue 23, respectively, are guided during approach of the individual stations by a cover and disc arrangement which includes an upper ring 25 and a lower ring 26 which are screwed together and which form a space 27 therebetween in which tongue 23 can slide during rotary movements of turntable 13. Both rings have a larger diameter than the turntable.

Figure 3:
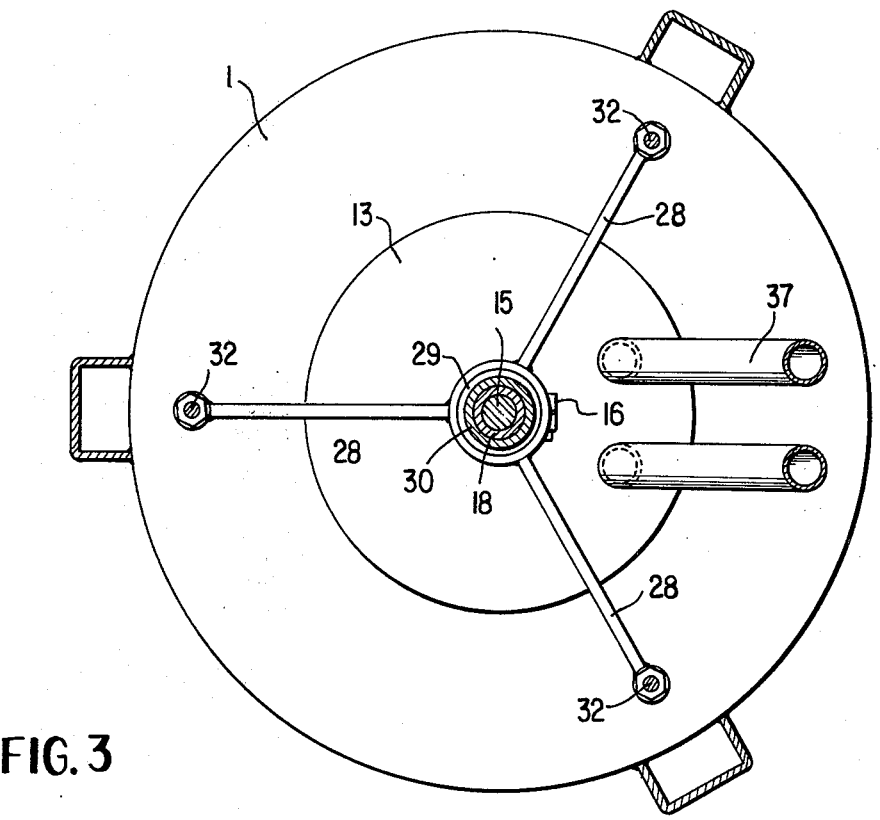
FIG. 3 is a cross-sectional top plan view taken along the plane 3—3 of FIG. 1 showing the detent member of the apparatus.

A detent 28 for controlling, i.e. limiting, the lifting movement of turntable 13 is fastened to the upper ring 25. Such lifting movements must be performed when the sample vessel 11 is to be pushed over the hollow needle 9. The detent 28 includes three arms, as can be seen in FIG. 3, and is guided by means of a guide sleeve 29 on a guide tube 30 which is seated on journal 18.

By means of three pneumatic cylinders 31, one per arm of detent 28, secured to plate 5, and by means of their associated rods 32, detent 28 can be moved along guide tube 30 between an abutment 33 at the lower end of guide tube 30 and a flange 34 at the upper end thereof. The path between abutment 33 and flange 34 for guide sleeve 29 is dimensioned so that the sample vessel 11 can be filled properly.

The passage for shaft 15 is sealed by means of 0-ring 36 which is accommodated in journal 18. The passages for rods 32 are sealed by means of lip seals accommodated in pneumatic cylinder 31 which is of known design, and may, for example, be Model DC 30–50 PPv S2 S3 of the company Fesfo, West-Germany.

The inner diameter of the upper ring 25 of the cover and disc arrangement 25, 26, 27 is dimensioned so that a removal pipe 37 for filled sample vessels 11 can be brought to the removal position 38. The removal pipe 37 and the inlet pipe 10 for the compressed air form a pneumatic conveying system for sample vessels. The discharge opening 39 of inlet 10 and the entrance opening 40 of removal line 37 are arranged in line with one another so that the sample vessel 11 can be blown by means of compressed air from inlet pipe 10 out of its holder 20, 24 and removed through removal pipe 37. This is achieved when the sample vessel 11 is, of course, disposed in the removal position which is aligned between the two pipes 10 and 37.

The removal pipe 37 passes into the outer chamber 42 through a hermetic flange connection 41 and cover plate 5. In order to be able to bring removal pipe 37 closer to or into a more centered position for removal, additional recesses (not shown in detail) may be provided in upper ring 25. A corresponding recess may also be provided in the filling position of holder 20, 24 where the sample vessel 11 is placed into the holder or the holding sleeve 20, respectively, by hand, by machine or through a further conduit system 43 from outer chamber 42.

Figure 4:
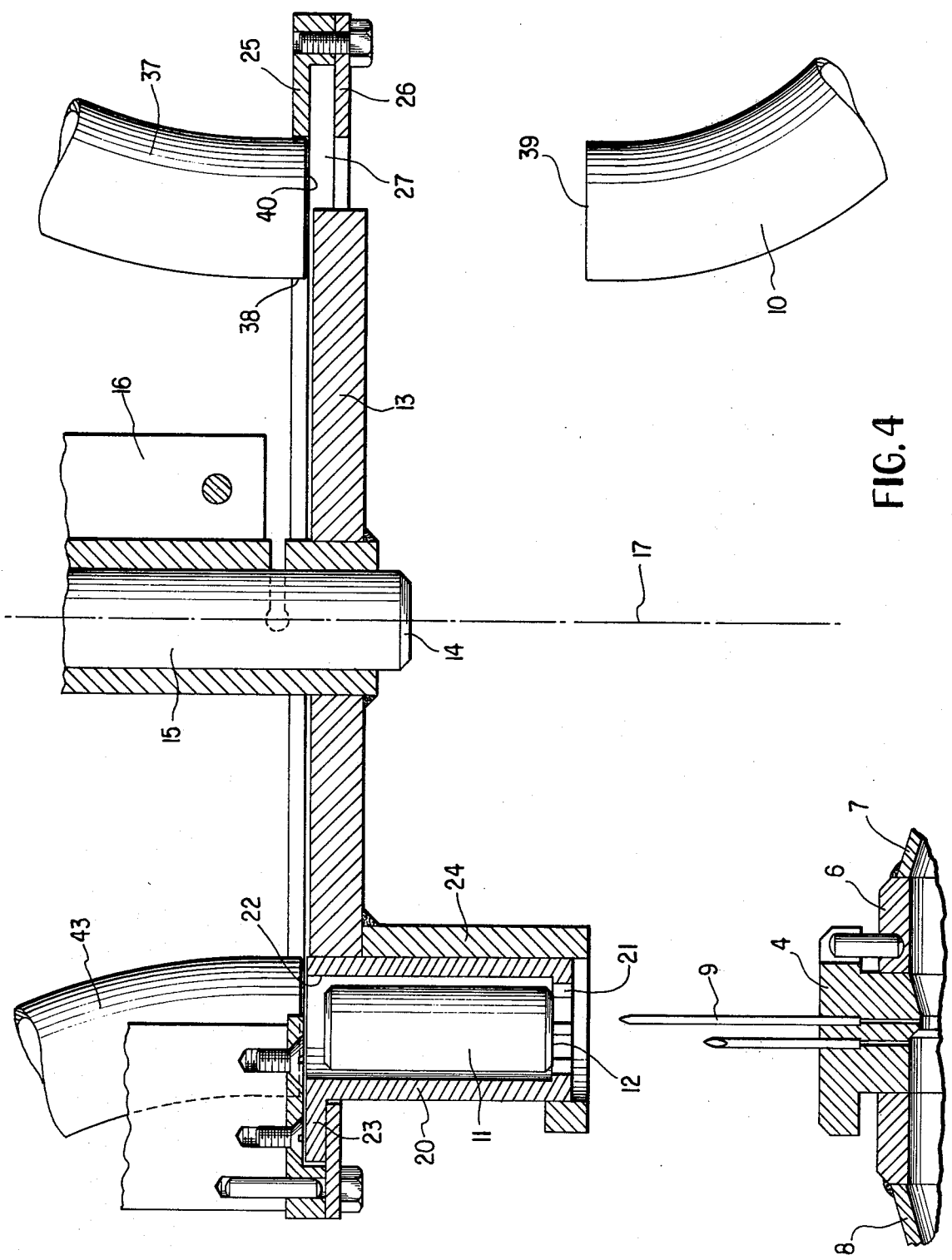
FIG. 4 shows a detail of the cover and disk arrangement.

In FIG. 4 a detail of the cover and disk arrangement is shown. During rotation the turntble 13 together with the sleeve 24 and the sleeve 20 for the sample vessel 11 is moved whereas the tongue 23 of sleeve 20 slides in the slot (space 27). The upper and the lower ring 25 and 26 together with the detent 28 remain fixed. During the vertical liftings the detent 28, the rings 25 and 26 and the sleeve 20 with the tongue 23 and the sample vessel 11 are moved but not the turntable 13 and the sleeve 24. In the removal position 38 the upper ring 25 has a cemicircle recess in which the pipe 37 is arranged to allow the sample vessel 11 being left out of the sleeve 20.

It will be understood that the above description of the present invention is susceptible to various modifications, changes and adaptations, and the same are intended to be comprehended within the meaning and range of equivalents of the appended claims.

What is claimed is:

1. In apparatus for taking samples of toxic and/or radioactive substances by introducing such substances into sample vessels, which apparatus includes a holder for holding such a vessel, at least one needle head filling system composed of upwardly pointing hollow needles for introducing a sample of one such substance into such vessel at a filling position, and inlet and outlet conduits for conveying vessels to or from the holder at a transfer position, the improvement wherein: said holder comprises a turntable having a sleeve for accommodating such sample vessel, said turntable being mounted to undergo rotary movement to convey a sample vessel in said sleeve between the filling and transfer positions, and an assembly of a cover and a disc between which said turntable is disposed and presenting a circular space for guiding said sleeve over said filling system, and said apparatus comprises a stand supporting said filling system below said holder, and a lifting device connected for imparting a translational movement to said holder to bring a vessel in said holder into operative association with said filling system, which translational movement is independent of the rotary movement of said turntable.

2. An arrangement as defined in claim 1 wherein there are a plurality of needle head filling systems disposed in a circle on said stand for permitting said sleeve holding a sample vessel to be lowered onto he hollow needles of a selected one of said filling systems.

3. An arrangement as defined in claim 1 wherein said apparatus further comprises a shaft supporting said turntable for rotary movement, and said holder further comprises a detent fastened to said cover and disc assembly and provided with a guide sleeve surrounding said shaft for permitting said detent to move parallel to the axis of said shaft to effect the translational movement of said holder, said detent being connected to said lifting device.

4. An arrangement as defined in claim 3 wherein said apparatus further comprises a circular switching table connected to said shaft for rotating said shaft and said turntable in order to bring a vessel to the different positions.

5. An arrangement as defined in claim 3 wherein said lifting device is a pneumatically operated device provided with pneumatically actuated rods connected to said detent.

6. An arrangement as defined in claim 5 further comprising a cover plate delimiting the space in which samples are taken, with said switching table and said lifting device being disposed above said cover plate.

7. An arrangement as defined in claim 1 wherein said turntable is provided with a retaining recess, said sleeve is provided with a laterally extending tongue which is held in said recess to secure it against rotation and is guided in said circular space.

8. In apparatus for taking samples of toxic and/or radioactive substances by introducing such substances into sample vessels, which apparatus includes a holder for holding such a vessel, at least one needle head filling system composed of upwardly pointing hollow needles for introducing a sample of one such substance into such vessel at a filling position, and inlet and outlet conduits for conveying vessels to or from the holder at a transfer position, the improvement wherein: said holder comprises a turntable having a sleeve for accommodating such sample vessel, said turntable being mounted to undergo rotary movement to convey a sample vessel in said sleeve between the filling and transfer positions; said apparatus comprises a stand supporting said filling system below said holder, and a lifting device connected for imparting a translational movement to said holder to bring a vessel in said holder into operative association with said filling system, which translational movement is independent of the rotary movement of said turntable; said inlet and outlet conduits are provided for removing sample vessels from said holder pneumatically after introduction of a sample therein, said inlet conduit is located below said turntable for supplying a pneumatic pressure medium, and said outlet conduit is located above said turntable for receiving a sample vessel propelled by the medium supplied via said inlet conduit said conduits having openings facing one another.

* * * * *